US012646311B2

(12) United States Patent
Xia et al.

(10) Patent No.: US 12,646,311 B2
(45) Date of Patent: Jun. 2, 2026

(54) METHOD AND APPARATUS FOR TRAINING A DEEP LEARNING BASED MODEL FOR HARMONIC IMAGING

(71) Applicant: CANON KABUSHIKI KAISHA, Tokyo (JP)

(72) Inventors: Ting Xia, Vernon Hills, IL (US); Jian Zhou, Vernon Hills, IL (US); Liang Cai, Vernon Hills, IL (US); Zhou Yu, Vernon Hills, IL (US)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/679,989

(22) Filed: May 31, 2024

(65) Prior Publication Data

US 2025/0371857 A1     Dec. 4, 2025

(51) Int. Cl.
*G06V 10/82* (2022.01)
*A61B 8/00* (2006.01)
*G06V 10/776* (2022.01)

(52) U.S. Cl.
CPC ............ *G06V 10/82* (2022.01); *A61B 8/5246* (2013.01); *A61B 8/5269* (2013.01); *G06V 10/776* (2022.01)

(58) Field of Classification Search
CPC .... G06V 10/82; G06V 10/776; A61B 8/5246; A61B 8/5269
See application file for complete search history.

(56) References Cited

U.S. PATENT DOCUMENTS

2023/0385643 A1* 11/2023 Rahman ................. G06N 3/082

FOREIGN PATENT DOCUMENTS

CN        113238987 B  * 11/2022  ......... G06F 15/7803
JP        2024-54939 A     4/2024

OTHER PUBLICATIONS

Rahman et al. ; Design of Novel Loss Functions for Deep Learning in X-ray CT ; Proc. Of SPIE vol. 12304 ; 2022 ; 6 Pages.
Fouad et al. ; A Single-Shot Harmonic Imaging Approach Utilizing Deep Learning for Medical Ultrasound ; IEEE Transactions on Ultrasonics, Ferroelectrics, and Frequency Control. vol. 70, Issue 4 ; Mar. 2023 ; 16 Pages.
Zhang et al. ; ATT Squeeze U-Net: A Lightweight Network for Forest Fire Detection and Recognition ; IEEE Access, vol. 9 ; Jan. 11, 2021 ; 13 Pages.

(Continued)

*Primary Examiner* — Dixomara Vargas
(74) *Attorney, Agent, or Firm* — Oblon, McClelland, Maier & Neustadt, L.L.P.

(57) ABSTRACT

An apparatus for training a model to perform harmonic imaging using ultrasound signals, the apparatus including processing circuitry configured to input first ultrasound data into a neural network model configured to generate and output second ultrasound data, determine a first error by applying a first filter to a difference between the second ultrasound data and target ultrasound data, determine a second error by applying a second filter, different from the first filter, to the difference between the second ultrasound data and the target ultrasound data, determine a loss value based on the determined first error and the determined second error, and update parameters of the neural network model based on the determined loss value to generate a trained neural network model.

20 Claims, 9 Drawing Sheets

(56)          References Cited

OTHER PUBLICATIONS

Wu et al. ; Quantized Convolutional Neural Networks for Mobile
Devices ; IEEE Xplore ; May 16, 2016 ; 11 Pages.
Zhang et al. ; ShuffleNet: An Extremely Efficient Convolutional
Neural Network for Mobile Devices ; Dec. 7, 2017 ; 9 Pages.
Cai et al. ; Enable Deep Learning on Mobile Devices: Methods,
Systems, and Applications ; ACM Trans. Des. Autom. Electron.
Syst., vol. 27, No. 3, Article 20 ; Apr. 25, 2022 ; 50 Pages.

* cited by examiner

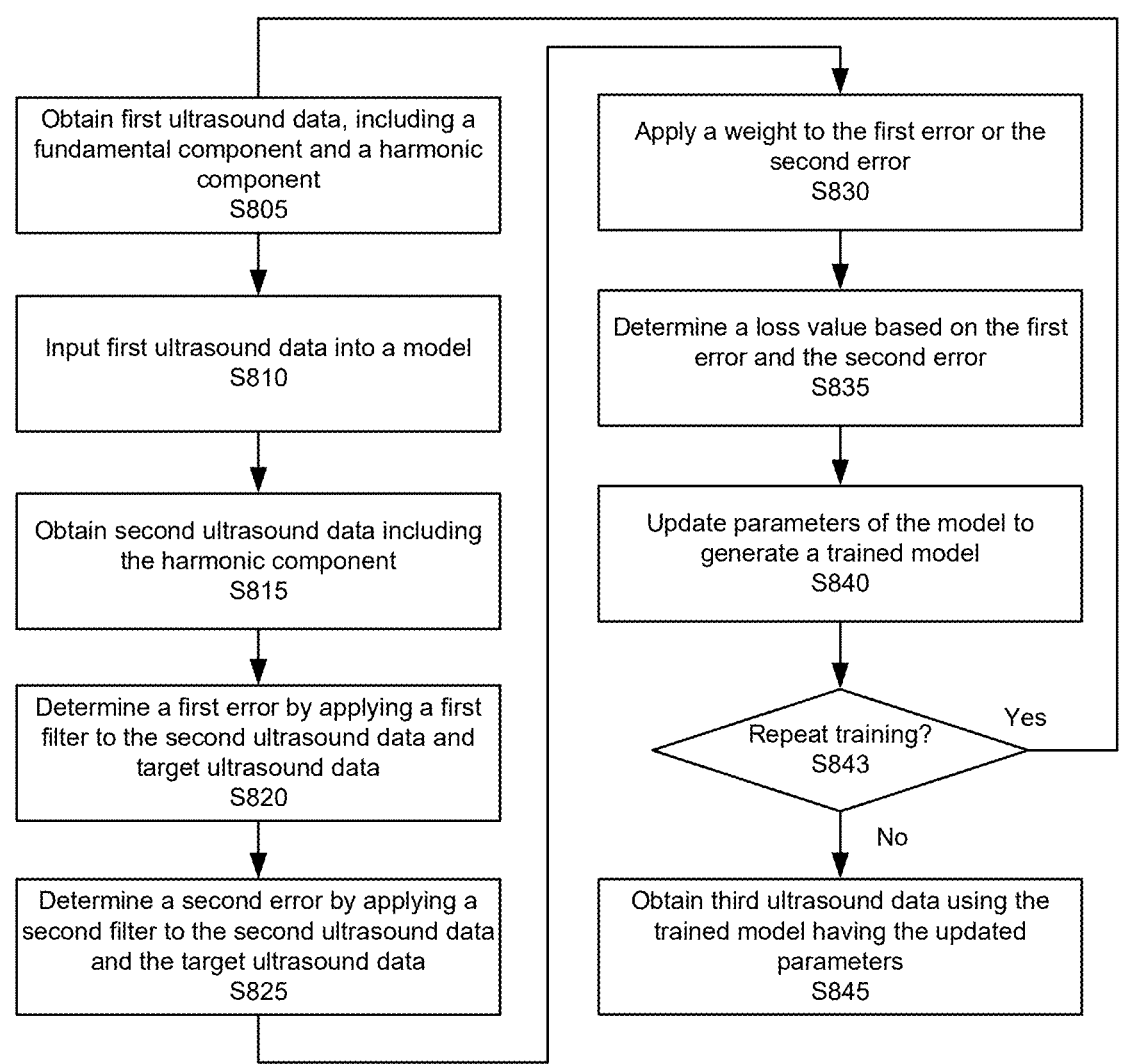
FIG. 8

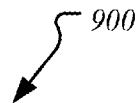

900

Obtain first ultrasound data, including a fundamental component and a harmonic component
S905

Convert the first ultrasound data into features having a frequency representation
S910

Input first ultrasound data in the frequency representation into a model
S915

Obtain second ultrasound data including the harmonic component in the frequency representation
S920

Determine a first error by applying a first filter to the second ultrasound data and target ultrasound data in a frequency representation
S925

Determine a second error in a frequency representation by applying a second filter to the second ultrasound data and the target ultrasound data
S930

Apply a weight to the second error
S935

Determine a loss value based on the first error and the second error
S940

Update a parameter of the model to generate a trained model
S945

Repeat training?
S948

Yes

No

Obtain third ultrasound data using the trained model having the updated parameters
S950

FIG. 9A

_901_

```
┌─────────────────────────────────┐
│  Obtain first ultrasound data,   │
│  including a fundamental          │
│  component and a harmonic         │
│  component                        │
│  S955                             │
└─────────────────────────────────┘
                 │
                 ▼
┌─────────────────────────────────┐
│  Input the obtained first         │
│  ultrasound data into a trained   │
│  neural network to obtain         │
│  second ultrasound data, wherein  │
│  the trained neural network was   │
│  trained using training input     │
│  data, corresponding target       │
│  data, and a loss function, the   │
│  loss function calculating a      │
│  loss value by determining a      │
│  first error by applying a first  │
│  filter to a difference between   │
│  the output ultrasound data       │
│  output from the neural network   │
│  in response to inputting the     │
│  training input data and the      │
│  target ultrasound data,          │
│  determining a second error by    │
│  applying a second filter,        │
│  different from the first filter, │
│  to the difference between the    │
│  output ultrasound data and the   │
│  target ultrasound data,          │
│  determining the loss value       │
│  using the loss function, which   │
│  is a function of the determined  │
│  first error and the determined   │
│  second error, and                │
│  updating parameters of the       │
│  trained neural network based on  │
│  the determined loss value        │
│  S960                             │
└─────────────────────────────────┘
                 │
                 ▼
┌─────────────────────────────────┐
│  Output the second ultrasound     │
│  data for displaying on a display │
│  S965                             │
└─────────────────────────────────┘
```

FIG. 9B

METHOD AND APPARATUS FOR TRAINING A DEEP LEARNING BASED MODEL FOR HARMONIC IMAGING

FIELD

This disclosure relates to a method and apparatus for ultrasound harmonic imaging. In particular, loss function designs for deep learning-based harmonic imaging are discussed.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

In ultrasound harmonic imaging, higher order harmonics can provide images with significantly reduced artifacts, an improved contrast-to-noise ratio, and improved lateral resolution. For some anatomic structures, such as blood vessels, a higher order harmonic image with improved contrast is desired, e.g., $3^{rd}$-order harmonic imaging can provide images with fewer artifacts and improved resolution compared with $2^{nd}$-order harmonic imaging.

Deep learning-based technology provides a possible solution to improve harmonic imaging with superior image quality and fast acquisition. To enhance the accuracy of the deep learning network, a common training method includes increasing the complexity of the trained network (e.g., depth and channel of the deep learning network). Therefore, the deep learning-based method for harmonic imaging can result in large/deep networks with intensive memory and computation power. The large memory and numerical costs can reduce their applicability in real-world use.

SUMMARY

A method and an apparatus for training a deep learning-based model or network for harmonic imaging that reduces model size while maintaining accuracy and memory efficiency is desired. The present disclosure relates to an apparatus for training a model to perform harmonic imaging using ultrasound signals, the apparatus including processing circuitry configured to input first ultrasound data into a neural network model configured to generate and output second ultrasound data, determine a first error by applying a first filter to a difference between the second ultrasound data and target ultrasound data, determine a second error by applying a second filter, different from the first filter, to the difference between the second ultrasound data and the target ultrasound data, determine a loss value based on the determined first error and the determined second error, and update parameters of the neural network model based on the determined loss value to generate a trained neural network model.

The disclosure additionally relates to a method for training a model to perform harmonic imaging using ultrasound signals, the method including inputting first ultrasound data into a neural network model configured to generate and output second ultrasound data; determining a first error by applying a first filter to a difference between the second ultrasound data and target ultrasound data; determining a second error by applying a second filter, different from the first filter, to the difference between the second ultrasound data and the target ultrasound data; determining a loss value based on the determined first error and the determined second error; and updating parameters of the neural network model based on the determined loss value to generate a trained neural network model.

Note that this summary section does not specify every embodiment and/or incrementally novel aspect of the present disclosure or claimed invention. Instead, this summary only provides a preliminary discussion of different embodiments. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein:

FIG. 8 shows a non-limiting example of a flow chart for a method of obtaining ultrasound data using a trained model, according to an embodiment of the present disclosure.

FIG. 9A shows a non-limiting example of a flow chart for a method of obtaining ultrasound data using a trained model with features having a frequency representation, according to an embodiment of the present disclosure.

FIG. 9B shows a non-limiting example of a flow chart for a method of training a model to perform harmonic imaging using ultrasound signals, according to an embodiment of the present disclosure.

DETAILED DESCRIPTION

Figure 1:
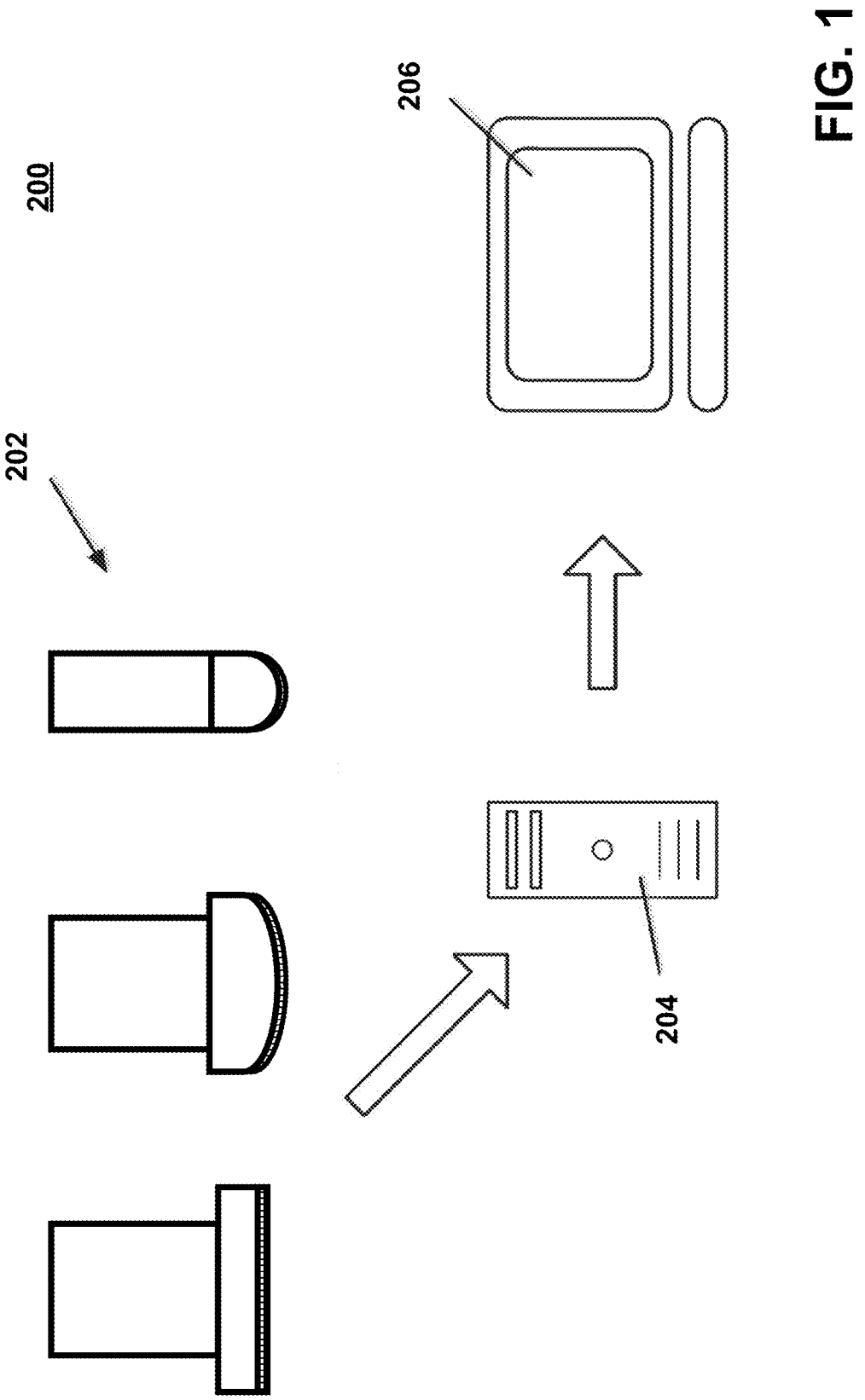
FIG. 1 is a system diagram for an ultrasound imaging system, according to an embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "top," "bottom," "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The system may be otherwise oriented (rotated 90 degrees or at other orientations) and the spatially relative descriptors used herein may likewise be interpreted accordingly.

The order of discussion of the different steps as described herein has been presented for clarity sake. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Ultrasound Tissue Harmonic Imaging (THI) is a signal processing technique in which an ultrasound beam insonates body tissues and generates harmonic waves from nonlinear distortion during a transmit phase of a pulse-echo cycle. Tissue harmonic images are obtained by transmitting a frequency spectrum by a probe and receiving a frequency spectrum that includes a fundamental echo in a band of fundamental frequencies (referred to herein as a fundamental frequency) as well as harmonics that originate in the body. In harmonic imaging, the harmonic images are obtained by collecting harmonic signals that are tissue generated, and filtering out the fundamental echo signals, resulting in sharper images. The harmonic signals (harmonics) are multiples of the fundamental frequency. Thus, transmitting a band of frequencies centered at a frequency $f$ will result in the production of harmonic frequency bands centered at $2f$, $3f$, $4f$, etc. (referred to as second-order harmonics, third-order harmonics, fourth-order harmonics, and so on for higher-order harmonics).

High-order harmonic imaging can provide images with fewer artifacts and improved resolution. However, high-order harmonic imaging (higher than second-order harmonics) has limited penetration depth due to the fast attenuation of high frequency signals. Second-order harmonics can penetrate to a greater depth compared to higher-order harmonics. However, second-order harmonic imaging suffers from more artifacts, and a reduced contrast-to-noise ratio in the near field. In the case of anatomic structures such as blood vessels, it is desired to obtain a high-order harmonic image having improved contrast.

In conventional ultrasound imaging, to obtain high-order harmonics, the ultrasound probe needs to send multiple pulses with opposite/desired phases sequentially into a tissue along the same line. Subsequently, the time duration of image acquisition is long, resulting in a low frame rate. However, a high frame rate is particularly important in cases where tissue movement occurs, as the movement can greatly impact the image quality. Also, the conventional ultrasound imaging for high-order harmonics is generally limited to the signals received by the probe. Filters may be used to filter out some frequency bands in order to focus on a desired frequency. However, filtering alone does not enhance the quality of the ultrasound images.

To achieve harmonic imaging, separation based on high-pass filtering, pulse inversion (PI), and power amplitude modulation (PAM) are three commonly used methods for harmonics extraction from received echo signals. However, linear filtering suffers from spectral leakage in overlapping frequency bands of the fundamental and the harmonics, as well as its performance dependence on the cutoff frequency, filter order, and algorithm. PI and PAM overcome the aforementioned limitations, but use two or more successive transmissions, resulting in a decreased frame rate and susceptibility to motion artifacts, which poses a tradeoff between the achievable frame rate and the desired image quality.

Another example process is differential tissue harmonic imaging (DTHI). In DTHI, two pulses are transmitted simultaneously at different frequencies, referred to as $f_1$ and $f_2$. In addition to their second harmonic frequencies ($2f_1$ and $2f_2$), among others, the sum and the difference of the transmitted frequencies ($f_2+f_1$ and $f_2-f_1$, respectively) are generated within the tissue. The second harmonic signal of the lower frequency ($2f_1$), and the difference frequency ($f_2-f_1$), are detected by the probe. Other generated frequency components do not fall within the bandwidth of the probe. By using DTHI, higher resolution, better penetration, and fewer artifacts can be achieved.

As described herein, deep learning-based technology can provide a solution to improve harmonic imaging with superior image quality and fast acquisition. Deep learning-based harmonic imaging training can include a low-quality lower-order input (e.g., IQ1 or IQ0, where IQ is in-phase and quadrature phase, or quadrature demodulated data) and a high-quality high-order harmonic target (e.g., IQ3 or denoised clean IQ3). During training, the simple multiplicative coefficients or other representations of neural interconnections are iteratively adjusted to minimize some measured ensemble error, or loss, between network-processed input data and their respective target data. As previously mentioned, to enhance the accuracy, a training method can increase the complexity of the trained network, (e.g., depth and channel of the deep learning network). Therefore, the deep learning-based method for harmonic imaging usually can result in large/deep networks with intensive memory and computation power.

In general, to speed up performance, hardware can be upgraded, quantization can be performed, or other model structures can be used, such as networks with group convolution, mobile nets, or model scaling. However, these options can be costly, time consuming, or require complex re-tooling. Instead, described herein is a training method that retains the simple backbone of the network structure and leverages the frequency-based nature in ultrasound harmonic imaging to design training methods that emphasize the high-frequency components during training.

FIG. 1 is a system diagram for an ultrasound imaging system. An ultrasound imaging system 200 can include any of a range of probes 202. Types of probes include convex, linear, and sector, as well as those designed for a special purpose. The signals received by a probe 202 are processed in a computer system 204. The ultrasound imaging system 200 can also include multi-harmonic compounding in which signals from individual beams are merged with overlapping data from adjacent beams.

Ultrasound images are created from sound waves at frequencies above the range audible to humans, typically on the order of 1-10 MHz or above. The probe 202 emits high frequency waves and records the reflected waves (fundamental frequency), bounced back from interfaces in the tissue, as a series of time-domain signals. One type of ultrasound image is a brightness image, also known as a B-mode image, which is a grayscale, intensity-based representation of the object.

The raw signals that the probe 202 receives are in the radiofrequency range and are known as radio frequency (RF) data. A series of signal processing steps are performed in the computer system 204 to convert from the RF data to the ultrasound image, such as a B-mode image. One preprocessing step is to demodulate the RF data to baseband and decimate the signal to reduce the bandwidth required to store the data. This new signal is referred to as an in-phase and quadrature phase (IQ) signal, and is typically represented with complex numbers. In this disclosure, the term IQ and RF data are used interchangeably since they both represent the raw data from the probe, but in different formats. In addition, embodiments of the deep neural networks of the present disclosure can be configured to take as input either the IQ data or an ultrasound image that is based on the IQ data.

The computer system 204 can be embedded in a portable ultrasound machine, can be a remote server, or can be a cloud service that is accessed through the Internet. The ultrasound imaging system 200 can include at least one display device 206 for displaying one or more ultrasound images. The display device 206 can be any of an LCD display, an LED display, an Organic LED display, etc. The display size and resolution are sufficient to display the ultrasound images that are output by the computer system 204.

Figure 2:
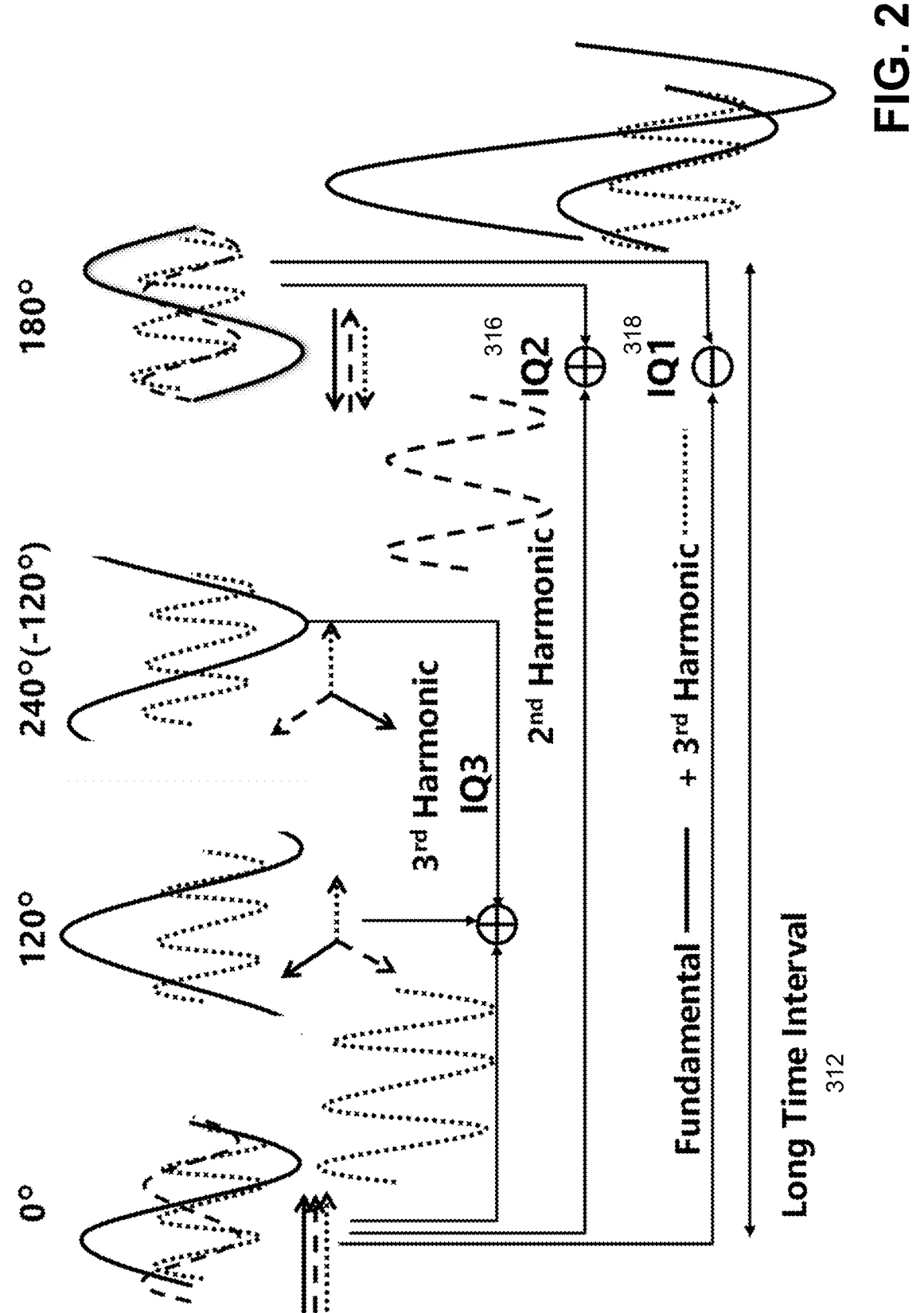
FIG. 2 illustrates a method of ultrasound tissue harmonic imaging, according to an embodiment of the present disclosure.

FIG. 2 illustrates an example method of ultrasound tissue harmonic imaging, according to an embodiment of the present disclosure. In order to obtain more signal in the ultrasound far field image, an image can be obtained for both second-order harmonics and third-order harmonics. As described above, one method is the DTHI method in which two pulses are transmitted simultaneously at different frequencies, referred to as $f_1$ and $f_2$. In addition to their second harmonic frequencies ($2f_1$ and $2f_2$), among others, the sum and the difference of the transmitted frequencies ($f_2+f_1$ and $f_2-f_1$, respectively) are generated within the tissue. The second harmonic signals 316 and 318 of the lower frequency ($2f_1$), and the difference frequency ($f_2-f_1$), respectively, are detected by the probe 202. However, the method involves a long time interval 312 for pulse generation. Subsequently, the frame rate is slow, leading to low-quality imaging, especially in cases of tissue motion.

Figure 3:
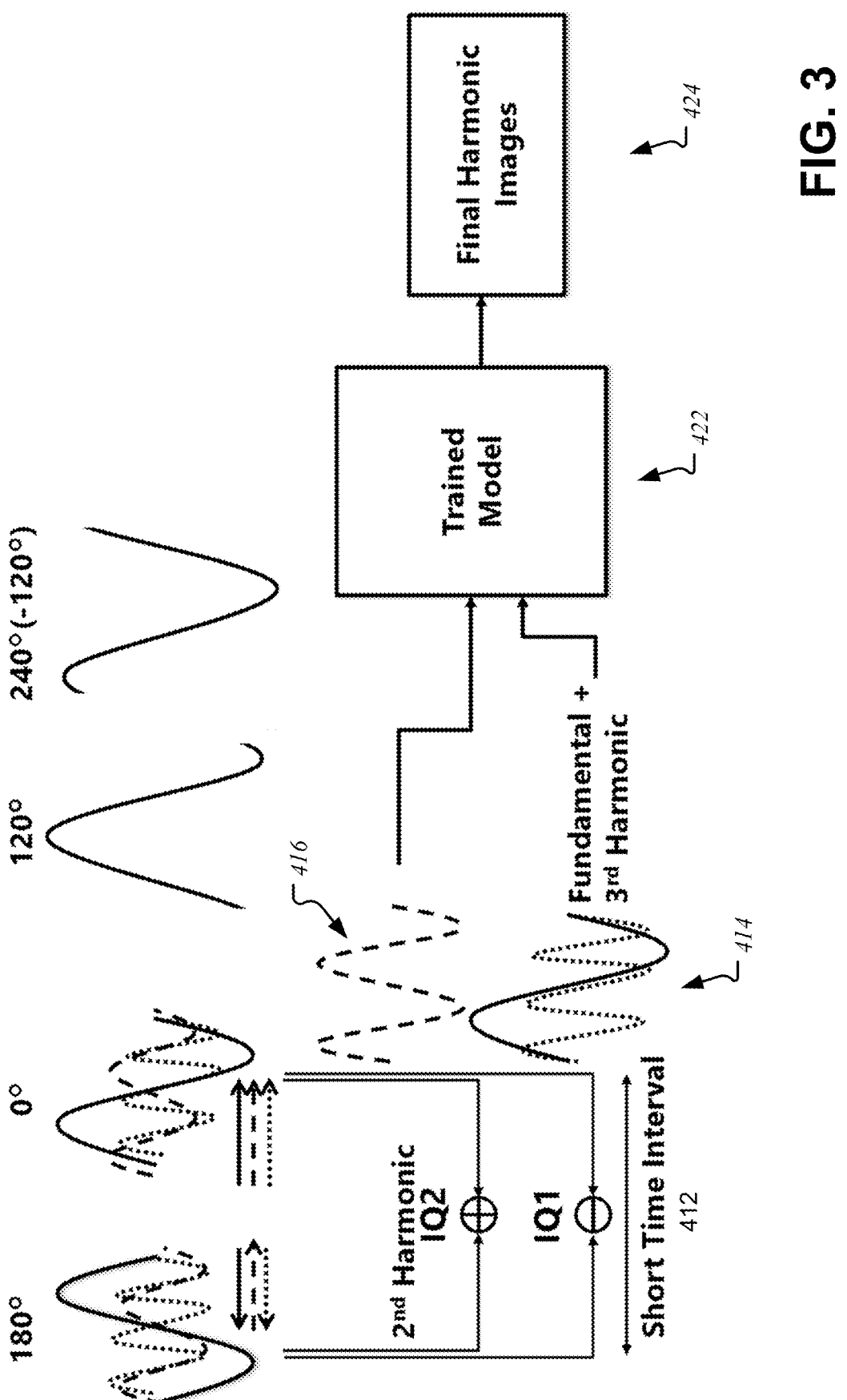
FIG. 3 illustrates a solution in ultrasound tissue harmonic imaging, according to an embodiment of the present disclosure.

FIG. 3 illustrates a neural network-based method of ultrasound tissue harmonic imaging, according to an embodiment of the present disclosure. In one embodiment, an imaging method involves pulse generation over a short time interval 412 by obtaining a signal that is a combination of fundamental ultrasound frequency and the third-order harmonic 414, and simultaneously obtaining the second-order harmonic 416. A deep neural network 422 can generate an estimated third-order harmonic from the combination signal. The deep neural network 422 can be trained to effectively generate a denoised second-order harmonic from the obtained second-order harmonic. In addition, the deep neural network 422 can be trained to effectively fuse the estimated third-order harmonic and the denoised second-order harmonic to generate an organ-specific fused image.

The short time interval 412 for pulse generation enables a reduction in the effects of motion and a reduction in artifacts. The deep neural network 422 can enable improved image quality in a shorter signal acquisition time.

In one embodiment, a deep learning-based framework is configured to input IQ data of various different combinations, as received by the probe 202, and subject to data processing steps in computer system 204, and to output a desired image with improved image quality, fewer near-field artifacts, improved contrast, and deeper penetration. The deep learning-based framework can directly use second- or third-order harmonics, or alternatively, use data containing fundamental frequencies. The input IQ data can include a combination of a fundamental frequency signal, second-order harmonics signal, and third-order harmonics signal (e.g., IQ0). The IQ data can include a combination of fundamental ultrasound frequency and third-order harmonics (e.g, IQ1). The input IQ data can also include just a second-order harmonics signal (e.g., IQ2), or just a third-order harmonics signal (e.g., IQ3). The input IQ data can also be other higher-order harmonics greater than third order.

The deep learning-based framework can undergo a training method for a particular target including desired harmonic data or a desired type of image. The framework can learn feature-awareness, depth-dependency, and be customized by considering patients with different body mass index (BMI) and/or demographic information. For example, the trained deep learning-based framework can be trained to output harmonic IQ data, or a depth-dependent fusion map.

The deep learning-based framework can be configured as a structure including a multilayer perceptron, a convolutional neural network such as U-net, or a fusion network. Convolutional neural networks (CNN) have been used in visual recognition tasks. CNNs can be trained with a large training set of images, for example, 1 million training images as in the ImageNet dataset. ImageNet has 8 layers and millions of parameters. Very deep convolutional networks can be used for large-scale image recognition.

One deep learning network architecture (U-Net) can be trained with far fewer images. Training with thousands of images is sometimes beyond the reach of typical biomedical tasks. The architecture of U-Net has an upsampling part and a large number of feature channels, which allows the network to propagate context information to higher resolution layers. Subsequently, the original U-Net architecture consists of a contracting path and an expansive path, in which an expansive path is more or less symmetric to a contracting path, giving the U-shaped architecture.

The contracting path follows the architecture of typical a convolutional neural network. It includes a repeated application of two 3×3 convolutions (unpadded convolutions), each followed by a rectified linear unit (ReLU) and a 2×2 max pooling operation with stride 2 for downsampling. At each downsampling step, the number of feature channels is doubled.

Every step in the expansive path includes an upsampling of the feature map followed by a 2×2 convolution ("up-convolution") that halves the number of feature channels, a concatenation with the correspondingly cropped feature map from the contracting path, and two 3×3 convolutions, each followed by a ReLU. At the final layer, a 1×1 convolution is used to map each 64-component feature vector to the desired number of classes.

Figure 4:
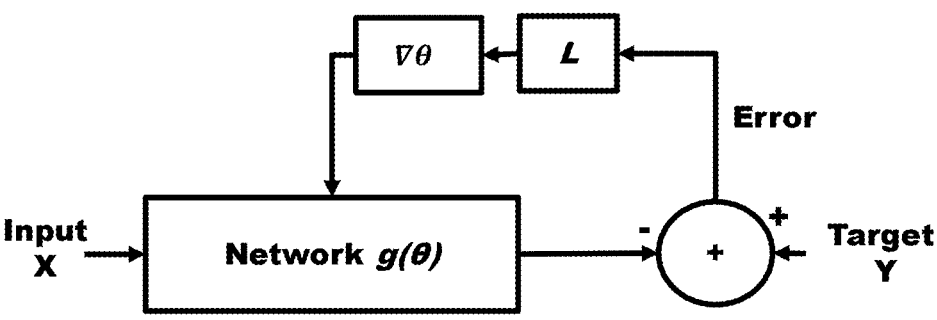
FIG. 4 is a schematic showing training of a neural network with a loss function, according to an embodiment of the present disclosure.

FIG. 4 is a schematic of the use of a loss function in training, according to an embodiment of the present disclosure. In one embodiment, the loss can be a measure of how well a deep learning model can predict the desired outputs from a given set of input targets. The loss function can also be known as a cost or objective function, and can be configured to quantify the difference between the actual values and the predicted (inferred) values by the model. As shown, the loss function can be represented by "L" in the process of training the neural network. Parameters governing system behavior can be denoted by θ. The gradient of the loss function's penalization of error (L), as a function of θ, can be used to improve the averaged match between a target and an output of the neural network during training.

When the variable k is used to index among training pairs, n to index entries in vectors $X_k$ and $Y_k$, and θ to represent the variable parameters of the network, the training optimization can be expressed as:

$$\hat{\theta} = \arg\min \sum_k L[X_k, Y_k, g_\theta(X_k)] \qquad (1)$$

Described herein, a loss function L in equation (1) can take the form:

$$L[S_k] \triangleq \Phi[f_1(S_k)] \qquad (2)$$

where $S_k$ is the error and Φ is a suitable error metric applied only within the passband of the filter $f_1$.

Figure 5:
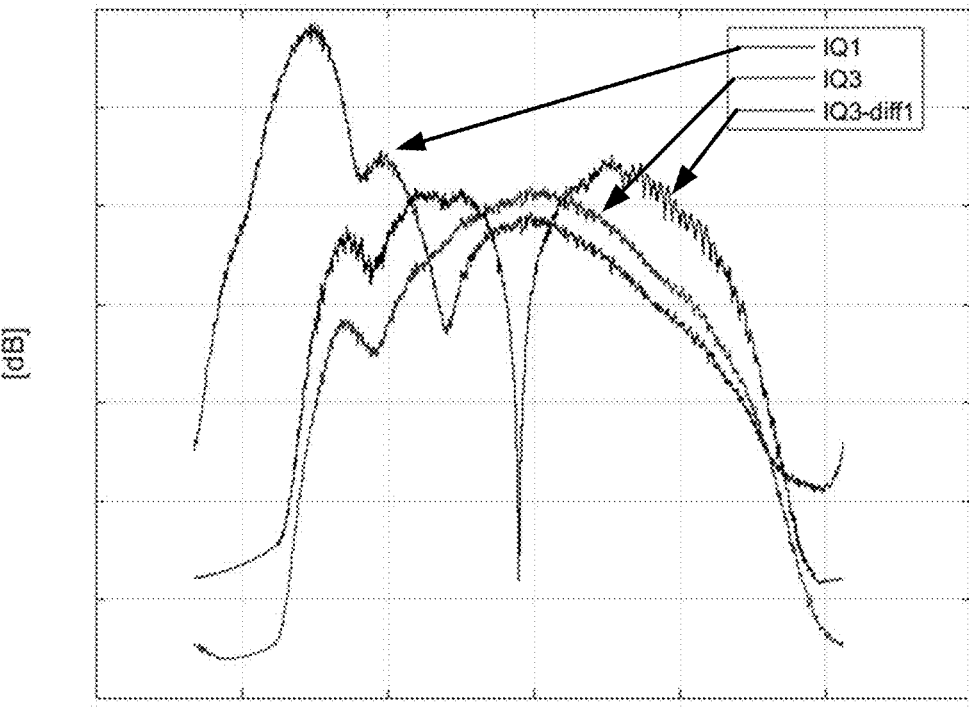
FIG. 5 is a graph of an input spectrum, an output spectrum, and a high pass filter, according to an embodiment of the present disclosure.

FIG. 5 is a graph of example spectra for designing a filter, according to an embodiment of the present disclosure. In one embodiment, the graph can include an input signal X (IQ1), a target signal Y (IQ3), and a designed filter $f_1$ (IQ3–diff1), which can be, for example, a high-pass filter in the frequency domain to emphasize the high frequencies of harmonic imaging during training.

In one embodiment, the filter $f_1$ can be a high-pass filter or a band-pass filter. Accordingly, the band-pass or high-pass components can be highlighted in the resulting high-order harmonic data. Similarly, a weighted sum for the final total loss can be applied, both penalizing a difference between network output and a target as a whole, and the corresponding frequency components. This can be expressed as:

$$L[S_k] \triangleq \Phi[\alpha f_1(S_k) + f_2(S_k)] \qquad (3)$$

$$S_k \triangleq Y_k - g_\theta(X_k) \qquad (4)$$

Figure 6:
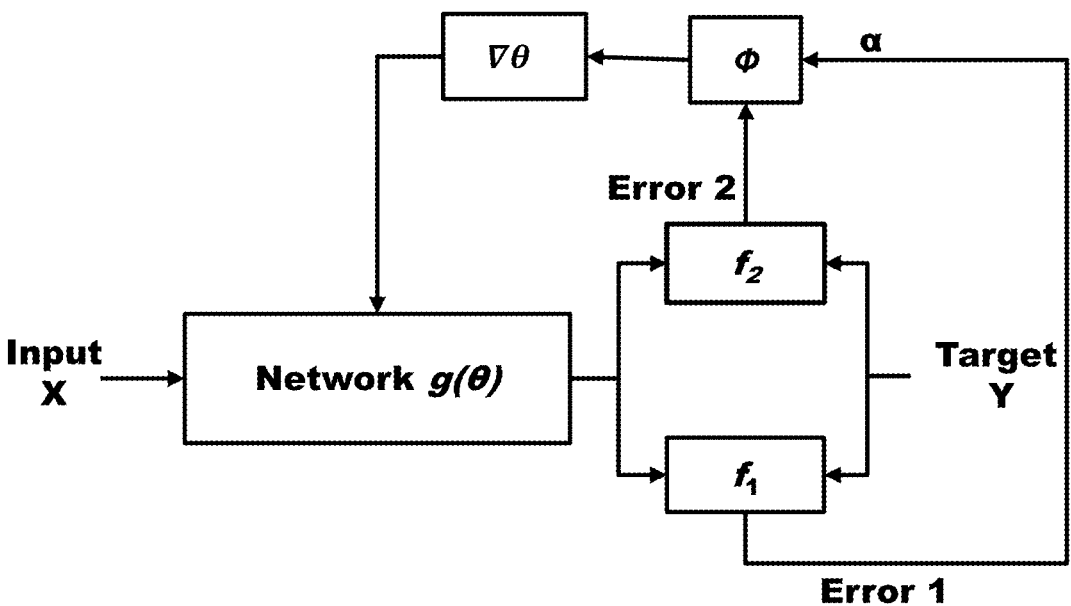
FIG. 6 is a schematic showing a weighted loss function, according to an embodiment of the present disclosure.

To this end, FIG. 6 is a schematic for a method of training a network, according to an embodiment of the present disclosure. In one embodiment, function $f_2$ can be another filter (e.g., an all-pass filter or a frequency-band-emphasis filter) or a function for B-mode calculation. Notably, the filter $f_1$ and the filter $f_2$ can be designed based on the particular application. For example, the filter $f_1$ can be a Sobel (operator or filter) or a Prewitt gradient edge-detection filter. The Sobel operator can perform a 2D spatial gradient measurement on an image and emphasize regions of high spatial frequency that correspond to edges. Typically, the Sobel filter can be used to find the approximate absolute gradient magnitude at each point in an input grayscale image. The weight(s) α can control the contribution from high-frequency components.

Referring back to FIG. 5, in one embodiment, the IQ3 curve can be the target during training. When using just a single loss L1, the single loss L1 does not emphasize the frequency component of the high frequency that is desired. Thus, a Sobel loss can be applied to IQ1 in FIG. 5 to emphasize the high-frequency components. Therefore, the loss is a weighted sum. As described in equation (3), the loss can be a weighted sum of the outputs of the filter $f_1$ and the filter $f_2$.

In one embodiment, the filter $f_2$ can be an all-pass filter, and thus a particular frequency band is not selected or targeted. As shown in equation (3), the weight α can apply to the filter $f_1$, which can be a Sobel loss, and the weight can be carefully adjusted to obtain an optimal Sobel weighted loss. The optimally Sobel weighted loss can result in improved results for the imaging. The Sobel filter can be a 2D filter including a pair of convolution kernels. The convolution kernels can be, for example, 3×3, 5×5, 7×7, etc.

As shown in FIG. 6, the input X (e.g., the IQ1 curve of FIG. 5) can be input into the network g(θ). The network can generate an inference output, which can be compared to a target output Y (e.g., the IQ3 curve of FIG. 5) to determine an error. That is, the error or difference between the inference output and the target output Y can be filtered via the filter $f_2$ and generate a second filtered error. Additionally or alternatively, the error or difference between the inference output and the target output Y can be filtered via the filter $f_1$ and generate a first filtered error. The first filtered error can additionally or alternatively be weighted by the weight α. The two filtered errors can be combined to generate a total error, which is used to adjust the variable parameters of the network. Alternatively, the filters $f_1$ and $f_2$ can provide respective error outputs based on inputs of the inference output and the target output Y. The filter $f_1$ can be at least one of a high-pass filter and a band pass filter. The filter $f_2$ can be at least one of an all-pass filter and some frequency-band emphasis filter. Therefore, the filter $f_1$ is different from the filter $f_2$. The weights a controls a contribution from high frequency components.

As previously described, in one embodiment, a deep learning-based framework can be configured to input IQ data of various different combinations, as received by the probe 202, and subject to data processing steps in computer system 204, and to output a desired image with improved image quality, fewer near-field artifacts, improved contrast, and deeper penetration. In one embodiment, the input data can be an ultrasound image, such as a brightness mode (B mode) image. In one embodiment, the input data can be complex data having a real part and an imaginary part, such as the IQ data. The deep learning-based framework can directly use second- or third-order harmonics, or alternatively, use data containing fundamental frequencies. The input IQ data can include a combination of a fundamental frequency signal, a second-order harmonics signal, and a third-order harmonics signal (IQ0). The IQ data can include a combination of fundamental ultrasound frequency and third-order harmonics (IQ1). The input IQ data can also include just a second-order harmonics signal (IQ2), or just a third-order harmonics signal (IQ3). The input IQ data can also be other higher-order harmonics greater than third order.

In one embodiment, the neural network model can be used to generate output ultrasound data. For example, after sufficient training and adjusting, input ultrasound data can be input into the neural network model to generate the output ultrasound data including the harmonic component.

Figure 7:
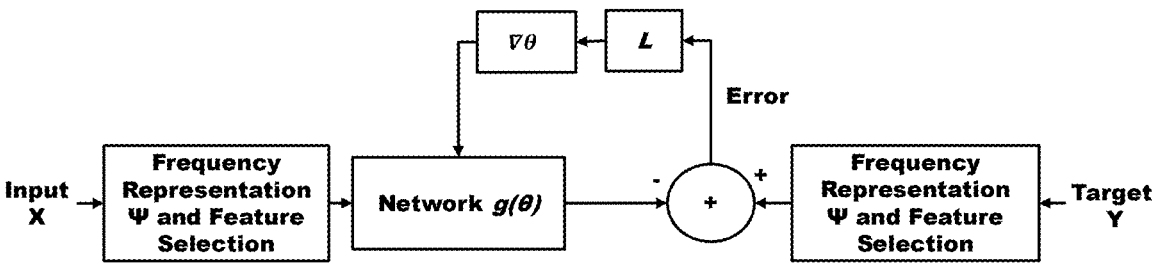
FIG. 7 is a schematic showing training of a neural network based on frequency represented features, according to an embodiment of the present disclosure.

FIG. 7 is a schematic for training a neural network using features represented in a frequency domain, according to an embodiment of the present disclosure. In one embodiment, the frequency representation can be emphasized during training. Previously, the contribution of the frequency components are considered in the loss function design, but not particularly emphasized. With this training strategy, the frequency components of the input and target data are first analyzed and represented by block function Y. The network can be trained to optimize the represented frequency features. During the inferencing stage, the output of the network can generate frequency representations, and the block function Y can be inversed from the frequency domain to the spatial domain.

Advantageously, compared to upgrading hardware for speeding up the processing times of large models, the described method is cost-effective and easier to implement. Compared to other network structure model simplification methods, the described method can use simple U-net as a backbone network, and with fewer coefficients while keeping high inference accuracy, better SNR ratio, and better image contrast.

For the loss function design, the described method provides flexibility depending on different applications, and will not increase inference time while keeping satisfactory performance. The described method can also maintain a high frame rate in real-time imaging, avoid suffering from motion artifacts, or avoid spectrum leakage in traditional harmonic imaging.

FIG. 8 shows a non-limiting example of a flow chart for a method 800 of obtaining ultrasound data using a trained model, according to an embodiment of the present disclosure.

In one embodiment, step S805 includes obtaining first ultrasound data. The first ultrasound data can include, for example, a fundamental component and a harmonic component.

In one embodiment, step S810 includes inputting the first ultrasound data into a model or neural network. The model or neural network can be configured to generate second ultrasound data as an output. The second output ultrasound data can be, for example, specific frequency components of the input first ultrasound data.

In one embodiment, step S815 includes obtaining second ultrasound data. The second ultrasound data can include, for example, a harmonic component.

In one embodiment, step S820 includes determining a first error by applying a first filter to a difference between the second ultrasound data and target ultrasound data.

In one embodiment, step S825 includes determining a second error by applying a second filter to the difference between the second ultrasound data and the target ultrasound data. The second filter can be different from the first filter.

In one embodiment, step S830 includes applying a weight to the first error or the second error, or both the first error and the second error.

In one embodiment, step S835 includes determining a loss value based on the determined first error and the determined second error. The first error, as previously mentioned, can be weighted. The second error, as previously mentioned, can be weighted in combination with the first error. The first error can also not be weighted while the second error is weighted.

In one embodiment, step S840 includes updating a parameter of the neural network model based on the determined loss value to generate a trained model.

In one embodiment, at step S843, the method 800 can be repeated again through to the step S840.

In one embodiment, step S845 includes obtaining third ultrasound data using the trained model having the updated parameters. The third ultrasound data can be, for example, an improved ultrasound image.

FIG. 9A shows a non-limiting example of a flow chart for a method 900 of obtaining ultrasound data using a trained model with features having a frequency representation, according to an embodiment of the present disclosure.

In one embodiment, step S905 includes obtaining first ultrasound data. The first ultrasound data can include, for example, a fundamental component and a harmonic component.

In one embodiment, step S910 includes converting the first ultrasound data into features having a frequency representation when the first ultrasound data is not in a frequency representation.

In one embodiment, step S915 includes inputting the first ultrasound data, in the frequency representation, into a model or neural network. The model or neural network can be configured to generate second ultrasound data as an output also in the frequency representation. The output second ultrasound data can be, for example, specific frequency components of the input first ultrasound data.

In one embodiment, step S920 includes obtaining second ultrasound data. The second ultrasound data can include, for example, a harmonic component. The second ultrasound data can be in the frequency representation.

In one embodiment, step S925 includes determining a first error by applying a first filter to the difference between the second ultrasound data and target ultrasound data, the target ultrasound data also being in a frequency representation.

In one embodiment, step S930 includes determining a second error by applying a second filter to the difference between the second ultrasound data and the target ultrasound data, the target ultrasound data also being in the frequency representation.

In one embodiment, step S935 includes applying a weight to the first error or the second error, or both the first error and the second error.

In one embodiment, step S940 includes determining a loss value based on the first error and the second error. The first error, as previously mentioned, can be weighted. The second error, as previously mentioned, can be weighted in combination with the first error. The first error can also not be weighted while the second error is weighted.

In one embodiment, step S945 includes updating a parameter of the model based on the determined loss value to generate a trained model.

In one embodiment, at step S948, the method 900 can be repeated again through to the step S945.

In one embodiment, step S950 includes obtaining third ultrasound data using the trained model having the updated parameters.

FIG. 9B shows a non-limiting example of a flow chart for a method 901 of training a model to perform harmonic imaging using ultrasound signals, according to an embodiment of the present disclosure.

In one embodiment, step S955 includes obtaining first ultrasound data.

In one embodiment, step S960 includes inputting the obtained first ultrasound data into a trained neural network to obtain second ultrasound data, wherein the trained neural network was trained using training input data, corresponding target data, and a loss function, the loss function calculating a loss value by determining a first error by applying a first filter to a difference between the output ultrasound data output from the neural network in response to inputting the training input data and the target ultrasound data, determining a second error by applying a second filter, different from the first filter, to the difference between the output ultrasound data and the target ultrasound data, determining the loss value using the loss function, which is a function of the determined first error and the determined second error, and updating parameters of the trained neural network based on the determined loss value.

In one embodiment, step S965 includes outputting the second ultrasound data for displaying on a display.

Figure 10:
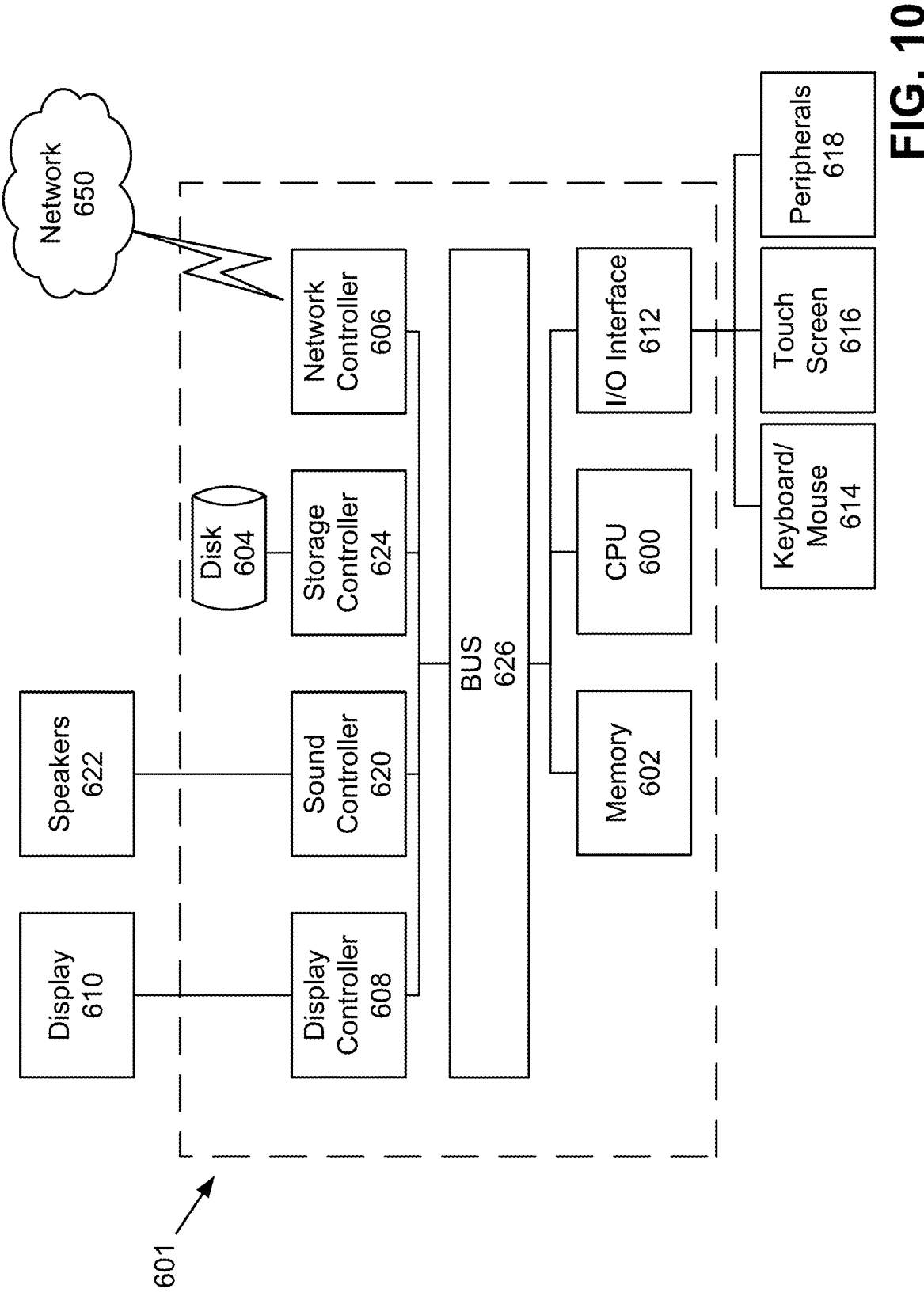
FIG. 10 is a schematic of a hardware configuration of a device for performing a method, according to an embodiment of the present disclosure.

Next, a hardware description of a device 601 according to exemplary embodiments is described with reference to FIG. 10. In FIG. 10, the device 601, which can be the above described processing devices, includes processing circuitry, as discussed above. The processing circuitry includes one or more of the elements discussed next with reference to FIG. 10. The device 601, may include other components not explicitly illustrated in FIG. 10 such as a CPU, GPU, frame buffer, etc. In FIG. 10, the device 601 includes a CPU 600 which performs the processes described above/below. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device 601 communicates, such as a server or computer.

Further, the claimed advancements may be provided as a utility application, background daemon, or component of an operating system, or combination thereof, executing in conjunction with CPU 600 and an operating system such as Microsoft Windows, UNIX, Solaris, LINUX, Apple MAC-OS and other systems known to those skilled in the art.

The hardware elements in order to achieve the device 601 may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the processes described above.

The device 601 in FIG. 10 also includes a network controller 606, such as an Intel Ethernet PRO network interface card from Intel Corporation of America, for interfacing with network 650, and to communicate with the other devices. As can be appreciated, the network 650 can be a public network, such as the Internet, or a private network such as an LAN or WAN network, or any combination thereof and can also include PSTN or ISDN sub-networks. The network 650 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

The device 601 further includes a display controller 608, such as a NVIDIA GeForce GTX or Quadro graphics adaptor from NVIDIA Corporation of America for interfacing with display 610, such as an LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners.

A sound controller 620 is also provided in the device 601 to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the device 601. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

In the preceding description, specific details have been set forth, such as a particular geometry of a processing system and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Embodiments of the present disclosure may also be as set forth in the following parentheticals.

(1) An apparatus for training a model to perform harmonic imaging using ultrasound signals, the apparatus including: processing circuitry configured to input first ultrasound data into a neural network model configured to generate and output second ultrasound data, determine a first error by applying a first filter to a difference between the second ultrasound data and target ultrasound data, determine a second error by applying a second filter, different from the first filter, to the difference between the second ultrasound data and the target ultrasound data, determine a loss value based on the determined first error and the determined second error, and update parameters of the neural network model based on the determined loss value to generate a trained neural network model.

(2) The apparatus of (1), wherein, in determining the loss value, the processing circuitry is further configured to apply a weight to the first error.

(3) The apparatus of either (1) or (2), wherein the processing circuitry is further configured to apply the first filter to the difference between the second ultrasound data and the target ultrasound data, the first filter being a high-pass filter or a band-pass filter.

(4) The apparatus of any one of (1) to (3), wherein the processing circuitry is further configured to apply the first filter to the difference between the second ultrasound data and the target ultrasound data, the first filter being a Sobel filter.

(5) The apparatus of any one of (1) to (4), wherein the processing circuitry is further configured to apply the second filter to the difference between the second ultrasound data and the target ultrasound data, the second filter being an all-pass filter.

(6) The apparatus of any one of (1) to (5), wherein the processing circuitry is further configured to input the first ultrasound data into the neural network model, the first ultrasound data including a fundamental frequency component and a third-order harmonic component.

(7) The apparatus of any one of (1) to (6), wherein the processing circuitry is further configured to convert the first ultrasound data into features having a frequency representation before inputting the first ultrasound data into the neural network model.

(8) The apparatus of any one of (1) to (7), wherein the processing circuitry is further configured to obtain the second ultrasound data in the frequency representation.

(9) The apparatus of any one of (1) to (8), wherein the processing circuitry is further configured to determine the first error and the second error using the target ultrasound data also in the frequency representation.

(10) The apparatus of any one of (1) to (9), wherein the processing circuitry is further configured to apply the weight to the first error to adjust a contribution from high-frequency components.

(11) A method for training a model to perform harmonic imaging using ultrasound signals, the method including inputting first ultrasound data into a neural network model configured to generate and output second ultrasound data; determining a first error by applying a first filter to a difference between the second ultrasound data and target ultrasound data; determining a second error by applying a second filter, different from the first filter, to the difference between the second ultrasound data and the target ultrasound data; determining a loss value based on the determined first error and the determined second error; and updating parameters of the neural network model based on the determined loss value to generate a trained neural network model.

(12) The method of (11), wherein the step of determining the loss value further comprises applying a weight to the first error.

(13) The method of either (11) or (12), wherein the first filter is a high-pass filter or a band-pass filter.

(14) The method of any one of (11) to (13), wherein the first filter is a Sobel filter.

(15) The method of any one of (11) to (14), wherein the second filter is an all-pass filter.

(16) The method of any one of (11) to (15), wherein the first ultrasound data includes a fundamental frequency component and a third-order harmonic component.

(17) The method of any one of (11) to (16), further comprising converting the first ultrasound data into features having a frequency representation before inputting the first ultrasound data into the neural network model.

(18) The method of any one of (11) to (17), further comprising obtaining the second ultrasound data in the frequency representation.

(19) The method of any one of (11) to (18), further comprising determining the first error and the second error using the target ultrasound data in the frequency representation.

(20) An apparatus for performing harmonic imaging using ultrasound signals, the apparatus including processing circuitry configured to obtain first ultrasound data, input the obtained first ultrasound data into a trained neural network to obtain second ultrasound data, wherein the trained neural network was trained using training input data, corresponding target data, and a loss function, the loss function calculating a loss value by determining a first error by applying a first filter to a difference between the output ultrasound data output from the neural network in response to inputting the training input data and the target ultrasound data, determining a second error by applying a second filter, different from the first filter, to the difference between the output ultrasound data and the target ultrasound data, determining the loss value using the loss function, which is a function of the determined first error and the determined second error, and updating parameters of the trained neural network based on the determined loss value, and output the second ultrasound data for displaying on a display.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

What is claimed is:

1. An apparatus for training a model to perform harmonic imaging using ultrasound signals, the apparatus comprising:
    processing circuitry configured to
        input first ultrasound data into a neural network model configured to generate and output second ultrasound data,
        determine a first error by applying a first filter to a difference between the second ultrasound data and target ultrasound data,
        determine a second error by applying a second filter, different from the first filter, to the difference between the second ultrasound data and the target ultrasound data,
        determine a loss value based on the determined first error and the determined second error, and
        update parameters of the neural network model based on the determined loss value to generate a trained neural network model, wherein
    the neural network model is a convolutional neural network (CNN).

2. The apparatus of claim 1, wherein, in determining the loss value, the processing circuitry is further configured to apply a weight to the first error.

3. The apparatus of claim 1, wherein the processing circuitry is further configured to apply the first filter to the difference between the second ultrasound data and the target ultrasound data, the first filter being a high-pass filter or a band-pass filter.

4. The apparatus of claim 1, wherein the processing circuitry is further configured to apply the first filter to the difference between the second ultrasound data and the target ultrasound data, the first filter being a Sobel filter.

5. The apparatus of claim 1, wherein the processing circuitry is further configured to apply the second filter to the difference between the second ultrasound data and the target ultrasound data, the second filter being an all-pass filter.

6. The apparatus of claim 1, wherein the processing circuitry is further configured to input the first ultrasound data into the neural network model, the first ultrasound data including a fundamental frequency component and a third-order harmonic component.

7. The apparatus of claim 1, wherein the processing circuitry is further configured to convert the first ultrasound data into features having a frequency representation before inputting the first ultrasound data into the neural network model.

8. The apparatus of claim 7, wherein the processing circuitry is further configured to obtain the second ultrasound data in the frequency representation.

9. The apparatus of claim 7, wherein the processing circuitry is further configured to determine the first error and the second error using the target ultrasound data also in the frequency representation.

10. The apparatus of claim 2, wherein the processing circuitry is further configured to apply the weight to the first error to adjust a contribution from high-frequency components.

11. A method for training a model to perform harmonic imaging using ultrasound signals, the method comprising:
    inputting first ultrasound data into a neural network model configured to generate and output second ultrasound data;
    determining a first error by applying a first filter to a difference between the second ultrasound data and target ultrasound data;
    determining a second error by applying a second filter, different from the first filter, to the difference between the second ultrasound data and the target ultrasound data;
    determining a loss value based on the determined first error and the determined second error; and
    updating parameters of the neural network model based on the determined loss value to generate a trained neural network model, wherein
    the neural network model is a convolutional neural network (CNN).

12. The method of claim 11, wherein the step of determining the loss value further comprises applying a weight to the first error.

13. The method of claim 11, wherein the first filter is a high-pass filter or a band-pass filter.

14. The method of claim 11, wherein the first filter is a Sobel filter.

15. The method of claim 11, wherein the second filter is an all-pass filter.

16. The method of claim 11, wherein the first ultrasound data includes a fundamental frequency component and a third-order harmonic component.

17. The method of claim 11, further comprising converting the first ultrasound data into features having a frequency representation before inputting the first ultrasound data into the neural network model.

18. The method of claim 17, further comprising obtaining the second ultrasound data in the frequency representation.

19. The method of claim 17, further comprising determining the first error and the second error using the target ultrasound data in the frequency representation.

20. An apparatus for performing harmonic imaging using ultrasound signals, the apparatus comprising:
    processing circuitry configured to
        obtain first ultrasound data,
        input the obtained first ultrasound data into a trained neural network to obtain second ultrasound data, wherein the trained neural network was trained using training input data, corresponding target data, and a loss function, the loss function calculating a loss value by
            determining a first error by applying a first filter to a difference between the output ultrasound data output from the neural network in response to inputting the training input data and the target ultrasound data,
            determining a second error by applying a second filter, different from the first filter, to the difference between the output ultrasound data and the target ultrasound data,
            determining the loss value using the loss function, which is a function of the determined first error and the determined second error, and
            updating parameters of the trained neural network based on the determined loss value, and
        output the second ultrasound data for displaying on a display, wherein
    the neural network model is a convolutional neural network (CNN).

* * * * *